United States Patent
Stout

(10) Patent No.: US 7,442,497 B2
(45) Date of Patent: Oct. 28, 2008

(54) METHODS OF DETERMINING CHRONIC HEPATITIS C INFECTION

(75) Inventor: Robert L. Stout, Overland Park, KS (US)

(73) Assignee: Clinical Reference Laboratory, Lenexa, KS (US)

( * ) Notice: Subject to any disclaimer, the term of this patent is extended or adjusted under 35 U.S.C. 154(b) by 0 days.

(21) Appl. No.: 10/051,253

(22) Filed: Jan. 18, 2002

(65) Prior Publication Data

US 2003/0152911 A1   Aug. 14, 2003

(51) Int. Cl.
- *C12Q 1/70* (2006.01)
- *C07K 16/10* (2006.01)
- *C07K 16/42* (2006.01)

(52) U.S. Cl. .................. 435/5; 435/7.1; 530/388.3; 530/391.1

(58) Field of Classification Search ........ 435/5
See application file for complete search history.

(56) References Cited

FOREIGN PATENT DOCUMENTS

WO   WO 00/26673   *   5/2000

OTHER PUBLICATIONS

Payan et al., Analyse quantitative des anticorps dirigés contre le virus de l'hépatite C (VHC): application au diagnostic d'infectio chronique par le VHC. Annales de Biologie Clinique 61(3):311-317, 2003.*

Teo et al (1992) J Clin Pathol;45:917-920.*

Lazizi et al (1992) J Clin Microbiology; 30,4:931-934.*

Brillanti et al (1993) Arch Virol (Suppl) 8: 213-218.*

Fabrizi et al (1996) Nephrol Dial Transplant. 11: 314-318.*

Fong et al (1996) Journal of Medical Virology. 49: 253-258.*

Cobas Amplicor Hepatitis C Virus Test, Version 2.0, 1/30-30/30; May 1999.

* cited by examiner

*Primary Examiner*—Bruce Campell
*Assistant Examiner*—Michelle Horning
(74) *Attorney, Agent, or Firm*—Hovey Williams LLP

(57) ABSTRACT

Methods for determining chronic hepatitis C infection are provided by the present invention. The methods generally involve determining the optical density of fluid samples which have tested positive for hepatitis C infection using an antibody-based assay. The optical density can then be used to determine in a predictive or probability-based manner whether the fluid sample contains chronic hepatitis C infection or whether the fluid sample merely contains antibodies to hepatitis C infection without resorting to costly molecular detection methods. Thus, the present invention permits differentiation between individuals who have cleared hepatitis C infection but still test positive in an antibody-based assay from individuals having chronic hepatitis C infection.

18 Claims, No Drawings

METHODS OF DETERMINING CHRONIC HEPATITIS C INFECTION

BACKGROUND OF THE INVENTION

1. Field of the Invention

The present invention is concerned with methods for detecting hepatitis C virus (HCV) infection. More particularly, the present invention is concerned with methods for detecting HCV infection and being able to differentiate between individuals having chronic HCV infection and those that have cleared the infection in blood samples that are older than 6 hours. Still more particularly, the present invention is concerned with identifying individuals who have cleared the HCV infection but still continue testing positive for antibody to HCV. Even more particularly, the present invention is concerned with performing an antibody-based assay on a fluid sample, which identifies individuals having antibodies to HCV, determining the optical density of the sample after the addition of the antibodies, and then performing an assay using molecular detection methods on those samples testing positive for antibodies in order to correlate optical density with samples testing positive using an antibody-based assay and using molecular detection methods. Most particularly, the present invention is concerned with performing an antibody-based assay for HCV in a fluid sample, determining the optical density of the sample and then using the optical density to predict the likelihood that sample was taken from an individual with chronic HCV infection.

2. Description of the Prior Art

Hepatitis C is a single stranded RNA virus belonging to the Flaviviridae family of virus. The virus is a principal cause of liver disease in the United States. Infection is detected by serology testing for antibody produced in response to the virus. Serology provides an inexpensive method for screening the population but this type of testing detects two groups of individuals. The first group includes individuals that were infected and recovered from the infection. The second group includes chronically infected individuals. But, the antibody test cannot differentiate between the two groups. Chronic infection occurs in 75% to 85% of infected individuals. Therefore, 15% to 25% of individuals that test positive for antibody to HCV have actually cleared the infection and are themselves not infectious. In order to overcome this deficiency, new molecular detection methods are replacing serology as the method of choice for detection of the virus. However, molecular detection methods are costly in comparison to antibody-based methods and therefore, such methods are recommended only for samples first testing positive in an antibody-based assay. In some applications the prohibitive cost of testing may be overcome by the pooling of multiple samples before molecular testing. Accordingly what is needed is a method of determining chronic HCV infection which does not require expensive molecular detection methods. What is further needed are methods of predicting which individuals have chronic HCV infection and which individuals have cleared the infection without resorting to molecular detection methods.

SUMMARY OF THE INVENTION

For patients infected with Hepatitis C virus, there is no clear relationship between the extent of liver disease or liver enzyme elevation(s) and the number of viral particles present in blood. This is very unusual for a viral infection. In contrast, the amount of hepatitis B virus in blood clearly correlates with the degree of inflammation in the liver and the degree of elevation of the liver transaminase enzymes in blood.

Acute or chronic HCV infection is detected with an antibody test. If the antibody test is positive the patient has been infected by HCV. However, while the antibody test documents exposure, it cannot determine if the individual is currently infected and is therefore infectious. Thus, antibody-based assays cannot distinguish between infectious individuals and non-infectious individuals based on positive assay results.

Hepatitis C viral particles can be detected in blood by testing for viral RNA specific sequences. The HCV RNA test is extremely sensitive and specific. However, the HCV RNA test is also very expensive. As a consequence, most blood samples are first assayed for the presence of antibodies to HCV. If the antibody test is positive, the person has or has had an infection by HCV. Seventy-five to 85% of antibody positive individuals are chronically infected and therefore are also positive for HCV RNA. Blood donors are routinely tested for antibody to HCV and such testing is done to reduce the risk of contamination of the blood supply. HCV RNA testing has also been shown to identify some HCV infected individuals that the antibody test has missed. Most of the samples which test negative for antibodies but test positive by HCV RNA testing are from individuals who are infected but have not yet produced detectable amounts of antibody.

Antibody level is a measure of how much antibody is present in blood. Surprisingly the present invention determined that the optical density produced in the test for antibody to HCV can be used to identify patients with a lower probability of being positive for HCV RNA. The lower the OD, the higher the probability that the sample is negative for HCV RNA and the more likely that the individual from whom the sample was taken does not have chronic HCV infection. Conversely, the higher the OD, the higher the probability that the sample will test positive for HCV RNA and the higher the probability that the individual from whom the sample was taken will have chronic HCV infection.

In one aspect of the present invention, a method of identifying individuals having a certain probability of having chronic HCV infection is provided. The method includes the steps of obtaining a fluid sample from an individual, performing an HCV antibody based assay on the sample, determining the optical density of the sample, and finally using the optical density to identify individuals having a certain probability of having chronic HCV infection. Depending upon the optical density of the sample, the probability that the individual from whom the sample was obtained is infected with chronic HCV can be obtained. Optical densities at or above a predetermined level will provide a certain desired probability that the individual has chronic HCV infection. Such a method could be used either before or, more preferably, after the fluid sample has been tested using an antibody-based assay for HCV antibodies. In preferred forms, the sample is first tested for antibodies to HCV and samples testing positive have their optical densities determined. Preferably, the HCV antibody-based assay includes the step of contacting the fluid sample with a quantity of HCV antibodies and a determination of whether the sample is positive or negative for HCV antibodies. Because certain optical densities provide different probabilities that an individual has chronic HCV infection, the desired level of probability should first be selected. Thereafter, all samples having an optical density correlated with that probability level would be used to identify individuals with that certain probability of HCV infection. Preferably, one would want to have a probability of at least 60% that samples having that predetermined optical density or higher came from individuals having chronic HCV infection. More preferably, a probability level of at least 70%, more preferably 80%, and still more preferably at least 90% will be selected. Even more preferably, the probability level will be at least 95% and most preferably, the probability level will be at least 97%. In the alternative, the optical density can be used to identify individuals having less than a 50% probability of having chronic HCV infection. In this manner, optical densities at or below a certain level will be classified as having less than a 50% probability that they were obtained from an individual having chronic HCV infection.

In another aspect of the present invention, a method is provided for predicting whether a fluid sample that tests positive for HCV antibodies will test positive for chronic HCV infection. The method generally involves the steps of determining the optical density of a fluid sample which includes sample fluid and antibodies to HCV. This optical density is then compared with standard optical density levels that are correlated with chronic HCV infection. Preferably, the measured optical density is compared with optical density ranges which correspond to certain probabilities of chronic HCV infection. In order to be effective, these ranges should permit predictions with at least 60% accuracy for any measured optical density. For example, if the optical density of a sample is less than 1.0, one can predict with at least 60% accuracy that there is less than about a 10% probability that the individual providing the sample has chronic HCV. Similarly, for optical densities less than 2.35, one can predict with at least 60% accuracy that there is less than about a 15% probability that the individual providing the sample has chronic HCV. However, when the optical density of the sample is greater than 2.35, the probability that the individual has chronic HCV is greater than about 70%. As the optical density rises, so does the probability that the individual providing the sample has chronic HCV infection. Accordingly, the probability that a sample having an optical density of 3.0 or greater was obtained by an individual having chronic HCV infection is greater than about 80%.

In another aspect of the present invention, a method is provided for determining the probability that an individual testing positive for HCV using an antibody-based test is chronically infected with HCV. Generally, the method involves obtaining a fluid sample from an individual, contacting this fluid sample with antibodies to HCV to form a solution, determining the optical density of the solution, and comparing the determined optical density of the solution with standard optical density values which are correlated with probabilities of chronic HCV infection. Preferably, the standard optical density values provide probabilities that the individual providing the sample has chronic HCV infection. As with the other preferred methods, the probability that the individual providing the sample has chronic HCV infection increases as the optical density of the sample increases. For example, when the optical density of a sample is less than about 1.0, the probability that the individual providing the sample has chronic HCV infection is less than about 20%. For samples having an optical density greater than 2.35, this probability rises to greater than about 70% and for samples having an optical density greater than about 3.0, the probability increases to greater than 80%.

Finally, the present invention provides a method for testing for chronic HCV infection which generally comprises the steps of obtaining a fluid sample, performing an antibody-based assay on the sample and measuring the optical density of the sample. The method may further include the step of using the measured optical density to determine whether the sample contains chronic HCV infection by comparing the optical density with a set of standard optical density values which are correlated with probabilities of chronic HCV infection.

Accordingly, the present invention overcomes the limitations of the prior art and provides an inexpensive and efficient method of predicting whether or not a sample of fluid contains chronic HCV infection without requiring expensive molecular detection methods. Using methods of the present invention, the optical density of a sample can be used to provide an indication of the probability that the sample contains chronic HCV infection and therefore was obtained from an individual having chronic HCV infection.

DETAILED DESCRIPTION OF THE PREFERRED EMBODIMENT

The following examples set forth preferred embodiments of the present invention. It is to be understood, however, that these examples are provided by way of illustration and nothing therein should be taken as a limitation upon the overall scope of the invention.

EXAMPLE 1

This example tested the detection of antibody to HCV in alanine aminotransferase (ALT) positive insurance applicant serum samples:

Materials and Methods:

Approximately 1,200 serum samples having ALT concentrations greater than 41 U/ml were assayed for the presence of antibodies to HCV using the Abbott HCV EIA 2.0 assay for HCV encoded antigen. The instructions for this assay were followed and are expressly incorporated by reference herein. Briefly, 10 µL of each calibrator specimen was dispensed into the bottom of an individual test tube before dispensing 400 µL of specimen diluent to each test tube. The specimen diluent contained TRIS buffer, 0.2% Triton X-100, protein lysate and animal sera preserved with 0.1% sodium azide. The resulting solution was mixed by gently tapping. Then, 200 µL of each diluted control, calibrator or specimen was transferred into the appropriate well of a reaction tray. The positive control contained inactivated human plasma reactive for anti-HCV and nonreactive for Hepatitis B surface antigen (HBsAg) and anti-HIV-1 with a minimum titer of 1:2, together with 0.1% of the preservative sodium azide. The negative control was human plasma deemed nonreactive by FDA licensed tests for HCV antibodies, antibodies to HIV and HbsAg, together with 0.1% of the preservative sodium azide. Next, a polystyrene bead coated with recombinant HCV antigens (c100-3, HC-31, and HC-34) was added to each well containing diluted control or specimen. A cover seal was applied and the tray tapped gently before incubating at 40±2° C. for 1 hour±5 minutes. The cover seal was then removed and discarded and each bead was washed. This completed the first incubation stage. The second incubation stage began by pipetting 200 µL of diluted enzyme labeled antibody to human immunoglobulin conjugate into each well containing a bead. The diluted conjugate contained 20% animal sera and TRIS buffer together with the preservatives gentamicin (0.01%) and thimerosal (0.01%). A new cover seal was applied and the tray tapped gently before incubating at 40±2° C. for 30±2 minutes in a water bath. The cover seal was removed and discarded and each bead was washed. Next, the beads were immediately transferred to properly identified assay tubes. The dispenser was primed immediately prior to dispensing the OPD (o-phenylenediamine.2HCl) substrate solution. The OPD substrate solution was prepared by transferring 5 μL of OPD diluent for each 12.8 mg OPD tablet to be dissolved. The OPD diluent was a citrate-phosphate buffer containing 0.02% hydrogen peroxide. A 300 μL quantity of freshly prepared OPD substrate solution was pipetted into two empty tubes and then into each tube containing a bead. The tubes were then covered and incubated at room temperature (15-30° C.) for 30±2 minutes. Finally, 1 ml of 1N sulfuric acid was added to each tube and agitated to mix. A water tube was then prepared by pipetting approximately 2 ml of distilled or deionized water into an empty tube. The instrument was blanked in mode zero using the water tube. Next, the absorbance of the substrate blank was determined and the mode for processing HCV EIA 2.0 was selected. The instrument was blanked with the valid substrate blank and the absorbance of the controls and specimens were determined in order to identify samples testing positive for HCV antibody.

Next, all samples testing positive for HCV antibody using this first antibody-based immunoassay were retested using a different ELISA test system (the ORTHO HCV version 3.0 HCV encoded antigen test system). The protocols described for this test system were followed and the teachings of this are expressly incorporated by reference herein. Briefly, the two components were brought to room temperature (15-30° C.) approximately 30 minutes prior to the beginning of the procedure. The liquid reagents were gently inverted several times while avoiding foaming. The incubator temperature was maintained at 37° C.±1° C. In addition to each specimen which tested positive using the first assay, one substrate blank, three negative controls, and two positive controls were included in the test. For the remaining wells, 200 μL of specimen diluent (phosphate-buffered saline with bovine protein stabilizers together with 0.1% 2-chloroacetamide as a preservative) was added. Next, 10 μL of the controls or specimens were added to the appropriate wells and the plate mixed by shaking for 5-10 seconds. The wells in the microwell strip were covered with a plate sealer and incubated at 37° C.±1° C. for 60 minutes±5 minutes. All wells were then washed five times with wash buffer (1×). For the first wash, the sample solutions were aspirated from the microwells, and the wells refilled with wash buffer. Approximately 20 seconds following addition of the wash buffer, the plate wells were again aspirated to remove the wash buffer. This aspirate/fill sequence was completed four additional times. After the fifth wash, the plate was inverted and firmly tapped on a clean paper towel to remove excess wash buffer. Next, 200 μL of conjugate was added to all of the wells except the wells for substrate blank. The conjugate contained anti-human IgG heavy chain (murine monoclonal) conjugated to horseradish peroxidase with bovine protein stabilizers, together with 0.02% thimerosal as a preservative. The wells in the microwell strip were again covered with a new plate sealer and incubated at 37° C.±1° C. for 60 minutes±5 minutes. During this incubation time 4 OPD substrate tablets were dissolved in substrate buffer as described in the package insert. After this second incubation, the wells were washed as previously described and 200 μL of the substrate solution was added to all of the wells. The solution was incubated at room temperature in the dark for 30 minutes±1 minute and then 50 μL of 4N sulfuric acid was added to all of the wells. The microwell strip plates were then read at a wavelength of 490 nm. HCV antibody positive samples were frozen for long-term storage. On average, samples were 6 days old at the time they were frozen.

Samples testing positive in both of the HCV antibody-based assays, were then tested for the qualitative presence of HCV RNA using the COBAS Amplicor HCV test, version 2.0 (Roche Diagnostics, Branchburg, N.J.). The samples may be up to 6 weeks old at the time of testing. The materials and methods of this test were followed and the same are incorporated by reference herein. To perform the COBAS Amplicor HCV test, the following reagents were prepared: HCV LYS, v2.0 (HCV Lysis reagent, version 2.0) which included Tris HCl buffer, 68% guanidine thiocyanate, 3% dithiothreitol, and less than 1% glycogen; HCV DIL, v2.0 (HCV Specimen Diluent, version 2.0) which includes Tris HCl buffer, Poly rA RNA (synthetic), EDTA, and 0.05% Sodium azide; HCV IC, v2.0 (HCV Internal Control, Version 2.0) which included Non-infectious in vitro transcribed RNA (microbial) containing HCV primer binding sequences and a unique probe binding region, Poly rA RNA (synthetic), EDTA, and 0.05% Sodium azide. These three reagents make up the specimen preparation kit. The controls kit included the following reagents: NHP (Negative Plasma (Human)) which includes human plasma, non-reactive by US FDA licensed tests for antibody to HCV, antibody to HIV-1/2, and HBsAg, and 0.1% ProClin® 300; HCV (−) C, v2.0 (HCV (−) control, version 2.0) which includes Poly rA RNA (synthetic), EDTA, 0.05% Sodium azide; and HCV (+) C, v2.0 (HCV (+) control, version 2.0) which includes non-infectious in vitro transcribed RNA (microbial) containing HCV sequences, Poly rA RNA (synthetic), EDTA, and 0.05% Sodium azide. The amplification kit included the following reagents: HCV MMX, v2.0 (HCV Master Mix, version 2.0) which included Bicine buffer, 16% DMSO, glycerol, <0.01% rTth DNA Polymerase (rTth pol, microbial), potassium acetate, <0.001% dATP, dCTP, dGTP, dUTP, <0.005% KY78 and KY80 primers (one is biotinylated), <0.01% AmpErase® (microbial), and 0.05% sodium azide; and HCV $Mn^{2+}$, v2.0 (HCV Manganese Solution, version 2.0) which included <2.0% Manganese, acetic acid, amaranth dye, and 0.05% sodium azide. The HCV detection kit included the following reagents: CX PS1, v2.0 (HCV Probe Suspension 1, version 2.0), which included MES buffer, <0.4% suspension of Dynabeads® (paramagnetic particles) coated with HCV-specific oligonucleotide capture probe, and 0.09% sodium azide; and CX4, v2.0 (HCV Probe Suspension 2, version 2.0) which included sodium phosphate buffer, 42.2% sodium thiocyanate, and 0.2% solubilizer. The detection reagents kit included the following reagents: DN4 (Denaturation Solution) which included 1.6% sodium hydroxide, EDTA, and Thymol blue; CN4 (Avidin-Horseradish Peroxidase Conjugate) which included Tris HCl buffer, <0.001% Avidin-horseradish peroxidase conjugate, Bovine serum albumin (mammalian), Emulsit 25 (Dai-ichi Kogyo Seiyaku Co., Ltd.), 0.1% Phenol, and 1% ProClin 150; SB3 (Substrate A) which included citrate solution, 0.01% hydrogen peroxide, and 0.1% ProClin 150; and SB (Substrate B) which included 0.1% 3,3',5,5'-Tetramethylbenzidine (TMB), and 40% Dimethylformamide (DMF). The conjugate detection reagent comprised the previously described CN4. The wash buffer (WB), was included as a 10×-wash concentrate which included phosphate buffer, sodium chloride, EDTA, <2% detergent, and 0.5% ProClin 300.

The following protocol was then used to test each sample. First, the specimens and a positive and negative control were prepared followed by reverse transcription of the target RNA to generate complimentary DNA (cDNA). An aliquot of each sample or control cDNA was amplified by PCR using HCV specific complimentary primers. Next, hybridization of the amplified produces to oligonucleotide probes specific to the target(s) was performed prior to the detection of the probe-bound amplified products by colorimetric determination.

For each 12 samples, including 10 patient specimens and 2 controls, an A-ring was placed on the A-ring holder. A working master mix was prepared by adding 100 μL of HCV $Mn^{2+}$, v2.0 to one vial of HCV MMX, v2.0. This master mix was inverted 10-15 times before adding 15 µL into each A-tube using a repeat pipettor. Next, A-rings containing the working master mix were placed in a resealable plastic bag and the bag was sealed securely. The A-rings were then moved to the pre-amplification-specimen preparation area and stored at 2-8° C. in this area until the specimen and control preparation was completed.

The working Lysis Reagent was prepared by vortexing the HCV IC v2.0 for 5-10 seconds before use. A 100 µL quantity of HCV IC v2.0 was added to one bottle of HCV Lys, v2.0 and mixed well. The remaining HCV IC 2.0 was discarded. Specimens were prepared by labeling one 1.5 ml screw-cap tube for each patient specimen and two additional tubes for the positive and negative controls. Then, 400 µL of working Lysis reagent was added to each of the labeled tubes and the tubes were then capped. Next, the controls were vortexed for 5-10 seconds before adding 200 µL of NHP to each of the two control tubes. These tubes were then capped and mixed well by vortexing. Next, 20 µL of NHP HCV (−) C, v2.0 was added to the tube labeled HCV (−) C containing working Lysis reagent. This tube was also capped and mixed well by vortexing. The tube labeled HCV (+) C containing working Lysis reagent had 20 µL NHP HCV (+) C, v2.0 added to the tube and the tube was capped and mixed well by vortexing. Next, 200 µL of each patient specimen was added to the appropriately labeled tube containing working Lysis reagent. These tubes were then capped and vortexed for 3-5 seconds. The specimen and control tubes were incubated in a dry heat block for 10 minutes at 60° C.+−2° C. and mixed well by vortexing. All caps were then removed from the tubes and 600 µL 100% isopropyl alcohol (at room temperature) was added to each tube. The tubes were recapped and vortexed for 3-5 seconds before incubating all tubes for two minutes at room temperature. An orientation mark was placed on each tube and the tubes were placed in the microcentrifuge with the orientation mark facing outward, so that the pellet will align with the orientation mark. The specimens and controls were centrifuged at maximum speed (12,500-16,000×g) for 15 minutes at room temperature. A new, fine-tip disposable transfer pipet was used to carefully remove and discard the supernatant from each tube, while being careful not to disrupt the pellet. As much liquid as possible was removed without disturbing the pellet. Next, 1.0 mL of room temperature 70% ethanol was added to each tube and the tubes were recapped and vortexed for 3-5 seconds. Again, the tubes were placed in a microcentrifuge with the orientation marks facing outward and centrifuged for 5 minutes at maximum speed (12,500-16,000×g) at room temperature. The tubes were carefully removed from the centrifuge. Next, a fine-tipped disposable transfer pipet was used to carefully remove and discard the supernatant without disturbing the pellet. As much of the supernatant as possible was removed due to the inhibition of the amplification reaction by ethanol. The tubes were then recapped and spun at maximum speed for 3-5 seconds. The residual supernatant was carefully removed without disturbing the pellet using a P200 pipettor fitted with a new tip for each tube. Next, 200 µL HCV DIL, v2.0 was added to each tube and the pellet was broken apart as much as possible with a P200 pipettor fitted with a P200 aerosol barrier tip. The mixture was vortexed vigorously for 10 seconds and the processed specimens were amplified within 3 hours of preparation. Next, 50 µL of each processed patient specimen and control was added to the appropriate A-tubes containing the working master mix and the tubes were capped. The position of the controls and specimens was recorded on the A-ring. Following preparation, specimens and controls in the A-rings were moved to the amplification/detection area.

The CX PS1, v2.0 was mixed well by vortexing prior to adding 2.5 ml CX PS1, v2.0 to one CX4, v2.0 cassette. The cassette was placed on the test specific reagent rack and the used CX PS1, v2.0 vial was discarded. For detecting the HCV internal control, IC PS1 was mixed well by vortexing. Next, 2.5 mL IC PS1 was added to one IC4 cassette. The cassette was placed on the test specific reagent rack and the used IC PS1 vial was discarded. The working substrate was prepared by pipetting 5 mL of SB into one SB3 cassette. In order to mix this solution, the solution was pipetted up and down. The empty SB vial was discarded. The working substrate was then placed in the generic reagent rack along with the DN4 and CN4 cassettes. The reagent racks were identified as generic or test specific using the AMPLILINK™ software as described in the Operator's Manual for the COBAS AMPLICOR Analyzer (Roche Diagnostics, Branchburg, N.J.). Inputting reagent positions and lot numbers into the instrument using the AMPLILINK™ software then configured the reagent racks. The reagent rack was then loaded onto the instrument. The D-cup rack was placed on the D-cup platform. One D-cup was required for each detection reaction and two D-cups were required for each cassette of working substrate in order to allow for blanking by the COBAS AMPLICOR Analyzer. The A-rings were placed into the thermal cycler segments of the analyzer and loaded using the AMPLILINK™ software. The sequence of samples and controls in the A-ring was entered in the AMPLILINK™ software. The cover of the thermal cycler was tightly closed. Finally, the COBAS AMPLICOR Analyzer was started as described in the Operator's Manual. The load check was verified before permitting the COBAS AMPLICOR Analyzer to automatically perform all additional steps.

The COBAS AMPLICOR Analyzer automatically performed reverse transcription, amplification, and detection. Results were expressed as absorbance value at 660 nm and samples were reported as positive or HCV RNA not detected. The negative control must read 0.1 OD 660nm or less for the batch to be acceptable. A patient sample is considered "HCV RNA not detected" if the OD 660 nm is less than 0.15 OD 660 nm. The positive control should have an OD 660 nm greater than 1.0. A sample is considered to be positive if it has an OD 660 nm of 0.15 or greater.

Results:

Comparison of data for the optical density of the HCV antibody and HCV RNA test is contained in Table 1. The optical densities for the two tests, RNA and anti(body), are arranged side-by-side. The columns are with a letter, A, B, ... etc, and represent the individual RNA A-rings.

TABLE 1

Comparison of the Optical densities for HCV antibody and HCV RNA tests.

| OD66 A RNA | OD45 anti | B RNA | anti | C RNA | anti | D RNA | anti | E RNA | anti | OD66 F |
|---|---|---|---|---|---|---|---|---|---|---|
| Contr | Contro | 0.53 | 2.5 | >4.00 | 2.5 | 4 | 2.5 | 0.006 | 0.74 | 0.36 |
| Contr | Contro | 1.29 | 2.5 | 0.004 | 0.82 | 0.00 | 2.5 | 0.006 | 1.49 | 0.06 |

TABLE 1-continued

Comparison of the Optical densities for HCV antibody and HCV RNA tests.

| | | | | | | | | | | |
|---|---|---|---|---|---|---|---|---|---|---|
| 3.04 | 3.0 | 0.65 | 2.5 | 0.006 | 2.5 | 3.69 | 2.5 | 0.006 | 0.69 | 0.01 |
| 3.09 | 3.0 | 1.67 | 2.48 | 4 | 2.5 | 4 | 2.5 | 4 | 3.00 | 1.55 |
| 3.15 | 3.0 | 0.49 | 2.5 | >4.00 | 2.5 | 3.69 | 2.5 | 0.006 | 0.71 | 0.47 |
| 3.99 | 3.0 | 0.21 | 2.36 | >4.00 | 2.47 | 4 | 3.0 | 0.004 | 2.11 | 1.51 |
| 3.99 | 3.0 | 3.15 | 2.5 | 3.52 | 2.5 | 0.00 | 2.31 | 4 | 3.00 | 1.24 |
| 0.003 | 2.06 | 0.27 | 2.5 | 3.52 | 2.5 | 3.69 | 3.00 | 4 | 2.50 | 1.67 |
| 2.82 | ND | 1.01 | 2.47 | 3.7 | 3.0 | 2.52 | 3.00 | 4 | 2.50 | 0.49 |
| NS | NS | 0.49 | 2.5 | 3.52 | 2.5 | 4 | 3.00 | 0.004 | 1.38 | 3.22 |

| | | | | | OD66 | | | | | |
|---|---|---|---|---|---|---|---|---|---|---|
| anti | G | anti | H | anti | I | anti | J | anti | K | anti |
| 2.50 | 3.22 | 2.50 | 3.7 | 3.00 | 2.06 | 3.00 | 0.003 | 1.39 | 1.92 | 3.00 |
| 2.50 | >4.0 | 2.50 | 3.52 | 3.00 | 0.36 | 3.00 | >4.00 | 3.00 | 0.1 | 3.00 |
| 2.50 | 0.00 | 0.98 | >4.0 | 3.00 | 0.25 | 3.00 | >4.00 | 3.00 | 0.47 | 2.50 |
| 1.53 | 0.00 | 2.31 | >4.0 | 3.00 | >4.0 | 0.82 | 3.22 | 3.00 | 1.93 | 2.50 |
| 2.50 | 3.7 | 2.50 | >4.0 | 3.00 | 1.26 | 3.00 | >4.00 | 3.00 | 3.7 | 3.00 |
| 2.50 | >4.0 | 3.00 | >4.0 | 3.00 | 2.67 | 3.00 | 3.4 | 3.00 | 3.15 | 2.50 |
| 2.50 | 2.12 | 3.00 | 0.00 | 1.38 | 0.69 | 2.50 | >4.00 | 3.00 | 1 | 2.42 |
| 2.50 | 3.7 | 3.00 | 3.7 | 3.00 | 1.06 | 2.50 | 3.7 | 3.00 | 2.11 | 2.50 |
| 2.50 | >4.0 | 3.00 | >4.0 | 3.00 | 0.63 | 2.50 | >4.00 | 3.00 | 1.54 | 2.50 |
| 1.18 | 3.7 | 3.00 | 3.4 | 2.50 | 2.16 | 2.50 | >4.00 | 2.50 | 1.33 | 3.00 |

Next, the results for HCV RNA and the antibody tests were analyzed to determine if there was a relationship. The statistical analysis is presented in Table 2.

TABLE 2

Summary of relationship between OD of the antibody test and HCV RNA positivity.

| | Antibody OD | | |
|---|---|---|---|
| RNA | 0.5-2.4 | 2.5-2.99 | 3.0> |
| Negative | 9 | 3 | 1 |
| Positive | 5 | 39 | 42 |
| Total | 14 | 42 | 43 |
| % Negative | 64.29 | 7.14 | 2.33 |

EXAMPLE 2

This example compared HCV PCR results for samples having an OD less than 2.5 with samples having an OD greater than 2.5.

Materials and Methods:

Eighteen fluid samples testing positive in an HCV antibody-based assay were analyzed for HCV RNA by PCR. The samples included the fluid samples having HCV antibodies added thereto, as described above. Nine of the samples had antibody OD readings of less than 2.5 and the remaining nine samples had antibody OD readings equal or greater than 2.5. For samples having an OD reading of less than 2.5, the readings varied between 0.797 to 1.764. Table 3 provides the results of this example.

Results:

TABLE 3

Detection of HCV RNA in antibody positive samples separated by antibody OD reading.

| Sample OD < 2.5 | PCR HCV RNA | Sample OD ≧ 2.5 | PCR HCV RNA |
|---|---|---|---|
| 0.898 | ND | 2.5 | 190000 |
| 0.797 | ND | 2.5 | 714000 |
| 1.578 | ND | 2.5 | 670000 |
| 1.019 | ND | 2.5 | 633000 |
| 1.115 | ND | 2.5 | 802000 |
| 1.070 | ND | 2.5 | 129000 |
| 0.830 | ND | 2.5 | 824000 |
| 1.764 | ND | 2.5 | 331000 |
| 1.198 | ND | 2.5 | 518000 |

For this example, ND indicates that HCV RNA was not detected. PCR HCV RNA is given in international units of HCV RNA per milliliter of sample. As shown by these results, all samples having an OD less than 1.764 were negative for HCV RNA and thus, each of the individuals from whom these samples were taken is non-infectious.

Discussion:

Optical density measurements for solutions containing fluid and HCV antibody are shown to be an effective indicator of whether a particular fluid sample contains HCV RNA without requiring an expensive HCV RNA test. Taking all of the test results from the examples, one should be able to predict that samples having an OD greater than 3.0 would test positive for HCV RNA with at least 70% accuracy. More preferably, the accuracy should be at least 80% and still more preferably at least 90%. Most preferably, using methods of the present invention, one should be able to predict that samples having an OD of at least 3.0 would be positive for HCV RNA with at least 97% accuracy. In other words, samples which first test positive for HCV antibody and which have an OD of at least 3.0 will test positive for HCV RNA at least 70% of the time, thereby indicating that 70% of such samples are obtained from individuals that have chronic HCV infection. Of the 42 samples which tested positive for HCV antibody and which had an OD measurement greater than 3.0, 41 subsequently tested positive for HCV RNA. Thus, without performing the HCV RNA test, one could predict with reasonable certainty whether or not an individual was infected with chronic HCV infection based upon the results from an antibody-based assay and a measurement of the OD of the solution which contains the sample and the antibodies to HCV.

Similarly, for samples testing positive in an HCV antibody-based assay and having an OD measurement of at least 2.5, one should be able to predict with at least 70% accuracy whether or not these samples would test positive for HCV RNA. More preferably, the accuracy should be at least 80% and still more preferably at least 90%. Most preferably, using methods of the present invention, one should be able to predict that samples having an OD of at least 3.0 would be positive for HCV RNA with at least 95% accuracy. The test results indicate that such accuracy is possible because of the 94 samples testing positive in the antibody-based assay and having an OD greater than 2.5, 89 tested positive for HCV RNA. Identical ranges apply for samples testing positive in the HCV antibody-based assay and having an OD of at least 2.36 as 94 of 99 samples subsequently tested positive for HCV RNA.

Samples having lower OD measurements can also be used to predict whether a sample will test negative for HCV RNA despite testing positive in an HCV antibody-based assay. For example, one should be able to predict that samples having an OD less than 1.0 would test negative for HCV RNA with at least 60% accuracy. More preferably, the accuracy should be at least 70% and still more preferably at least 80%. Most preferably, using methods of the present invention, one should be able to predict that samples having an OD of less than 1.0 would be negative for HCV RNA with at least 88% accuracy. Taking the results from the examples of this application, such predictions were shown possible in that 8 of 9 samples testing positive in the antibody-based assay and having OD measurements of less than 1 tested negative for HCV RNA. Similarly, samples having an OD measurement less than 1.5 or 2.35 and testing positive in an antibody-based assay were also negative for HCV RNA 88% of the time (16/18 and 22/25, respectively).

I claim:

1. A method of determining the probability of whether or not an individual has chronic HCV infection or has cleared said infection comprising the steps of:
   obtaining a fluid sample from the individual;
   performing an antibody-based assay on said sample, said assay including contacting said sample with a plurality of different HCV antigens reactive with different antibodies and detecting interactions between the antigens and antibodies from the sample;
   determining the optical density of said sample after said antibody-based assay is performed and with said plurality of different HCV antigens present in said sample; and
   using the optical density to determine the probability of whether the individual has chronic HCV infection by comparing the determined optical density with a correlation curve based on the optical densities of fluid samples in combination with HCV antigen from HCV antibody-based assays from individuals having chronic HCV infection and individuals that have cleared the HCV infection but still test positive for HCV antibodies,
   said method permitting a prediction having at least an 80% probability that the individual providing said fluid sample has chronic HCV infection when said optical density is greater than about 3.0 at 450 nm in comparison to a negative control which must have an optical density of 0.1 or less at 660 nm.

2. The method of claim 1, said performing step including the step of contacting said sample with a quantity of HCV antigen.

3. The method of claim 1, said performance of said antibody-based assay providing results indicating whether said sample is antibody positive or antibody negative.

4. The method of claim 1, said prediction having at least a 90% probability that the individual providing said fluid sample has chronic HCV infection.

5. The method of claim 1, said prediction having at least a 95% probability that the individual providing said fluid sample has chronic HCV infection.

6. The method of claim 1, said prediction having at least a 97% probability that the individual providing said fluid sample has chronic HCV infection.

7. The method of claim 1, said method permitting a prediction that the individual has a probability of less than 50% of having chronic HCV infection.

8. A method of determining the probability of whether an individual has chronic HCV infection or has cleared said HCV infection, wherein said individual has provided a first fluid sample comprising biological fluid testing positive for HCV antibodies from a first HCV antibody assay capable of detecting more than one HCV antibody and having a plurality of different HCV antigens reactive with different antibodies therein, said method comprising the steps of:
   (a) measuring the optical density of a second fluid sample, said second fluid sample comprising (i) a portion of said first fluid sample prior to conducting said HCV antibody assay, and (ii) a plurality of different HCV antigens reactive with different antibodies from a second HCV antibody assay;
   (b) correlating said measured optical density with a predetermined standard optical density value derived from individuals known to have chronic HCV infection; and
   (c) determining the probability that the individual providing the first fluid sample has chronic HCV infection or has cleared said infection based on said correlation,
   wherein said determining step includes the step of comparing said measured optical density with optical density ranges corresponding to certain probabilities that the individual has chronic HCV infection.

9. The method of claim 8, said certain probability that the individual has chronic HCV infection being less than about 10% when said measured optical density is less than 1.0 at 450 nm in comparison to a negative control which must have an optical density of 0.1 or less at 660 nm.

10. The method of claim 8, said certain probability that the individual has chronic HCV infection being less than about 15% when said measured optical density is less than 2.35 at 450 nm in comparison to a negative control which must have an optical density of 0.1 or less at 660 nm.

11. The method of claim 8, said certain probability that the individual has chronic HCV infection being greater than about 70% when said measured optical density is greater than about 2.35 at 450 nm in comparison to a negative control which must have an optical density of 0.1 or less at 660 nm.

12. The method of claim 8, said certain probability that the individual has chronic HCV infection being greater than about 80% when said measured optical density is greater than 3.0 at 450 nm in comparison to a negative control which must have an optical density of 0.1 or less at 660 nm.

13. A method of determining the probability that an individual testing positive for HCV infection using an antibody-based assay capable of detecting more than one HCV antibody is chronically infected with HCV or has cleared said infection, said method comprising the steps of:

obtaining a fluid sample from the individual;

contacting said fluid sample with a plurality of different HCV antigens reactive with different antibodies to form a solution;

determining the optical density of said solution having said plurality of different antigens therein;

comparing said determined optical density with a set of standard optical density values correlated with probabilities of chronic HCV infection; and determining the probability of whether or not the individual has chronic HCV or has cleared said infection based on said comparison, wherein said comparing step includes the step of using said standard optical density values to provide said probability that said individual has chronic HCV infection.

14. The method of claim 13, said probability increasing as said determined optical density increases.

15. The method of claim 13, said probability being less than 20% when said determined optical density is less than about 1.0 at 450 nm in comparison to a negative control which must have an optical density of 0.1 or less at 660 nm.

16. The method of claim 13, said probability being less than 20% when said determined optical density is less than about 2.35 at 450 nm in comparison to a negative control which must have an optical density of 0.1 or less at 660 nm.

17. The method of claim 13, said probability being greater than 70% when said determined optical density is more than about 2.35 at 450 nm in comparison to a negative control which must have an optical density of 0.1 or less at 660 nm.

18. The method of claim 13, said probability being greater than about 80% when said determined optical density is more than about 3.0 at 450 nm in comparison to a negative control which must have an optical density of 0.1 or less at 660 nm.

* * * * *